(12) United States Patent
Pacheco et al.

(10) Patent No.: US 9,533,121 B2
(45) Date of Patent: Jan. 3, 2017

(54) COMPONENTS AND METHODS FOR ACCOMMODATING GUIDEWIRE CATHETERS ON A CATHETER CONTROLLER SYSTEM

(71) Applicant: Catheter Precision, Inc., Ledgewood, NJ (US)

(72) Inventors: Robert Pacheco, Bayside, NY (US); Steve Foley, Kerrville, TX (US)

(73) Assignee: Catheter Precision, Inc., Budd Lake, NJ (US)

( * ) Notice: Subject to any disclaimer, the term of this patent is extended or adjusted under 35 U.S.C. 154(b) by 390 days.

(21) Appl. No.: 13/777,708

(22) Filed: Feb. 26, 2013

(65) Prior Publication Data
US 2014/0243742 A1     Aug. 28, 2014

(51) Int. Cl.
*A61M 25/01*     (2006.01)
*A61M 25/09*     (2006.01)
*A61B 17/00*     (2006.01)

(52) U.S. Cl.
CPC ........... *A61M 25/0113* (2013.01); *A61B 34/30* (2016.02); *A61M 25/09041* (2013.01); *A61B 2017/00212* (2013.01); *A61B 2034/301* (2016.02)

(58) Field of Classification Search
CPC .................. A61M 25/09041; A61M 25/0113; A61B 19/2203; A61B 2019/2242; A61B 2019/22011; A61B 2017/00212; A61B 25/09; A61B 2025/09116; A61B 2025/09125; A61B 2210/1092
USPC ............ 604/95.01–95.05, 117; 600/585, 424
See application file for complete search history.

(56) References Cited

U.S. PATENT DOCUMENTS

| | | | |
|---|---|---|---|
| 4,549,538 A | 10/1985 | Schadrack, III et al. | |
| 4,721,123 A | 1/1988 | Cosentino et al. | |
| 5,649,956 A | 7/1997 | Jensen et al. | |
| 5,810,880 A | 9/1998 | Jensen et al. | |

(Continued)

FOREIGN PATENT DOCUMENTS

| | | |
|---|---|---|
| WO | 2005087128 A1 | 9/2005 |
| WO | 2007008967 A2 | 1/2007 |
| WO | 2009092059 A3 | 7/2009 |

OTHER PUBLICATIONS

WIPO, International Preliminary Report on Patentability; PCT/US2006/027024; Jan. 16, 2008; 8pgs.

(Continued)

*Primary Examiner* — Imani Hayman
*Assistant Examiner* — Hamza Darb
(74) *Attorney, Agent, or Firm* — The Marbury Law Group, PLLC (57) ABSTRACT

Various embodiments provide systems and methods for controlling a catheter with a catheter positioning device by using a remote controller and a guidewire control mechanism that may be used to draw a guidewire through a catheter coupled with the catheter positioning system. As the catheter is advanced over the guidewire by the catheter positioning device, the guidewire control mechanism may draw the guidewire away, such as collecting any slack on the guidewire. In further embodiments, the guidewire control mechanism may match the speed at which the guidewire is drawn to the speed at which the catheter advances and thereby maintain the position of the guidewire relative to the patient.

14 Claims, 10 Drawing Sheets

(56) References Cited

U.S. PATENT DOCUMENTS

| | | |
|---|---|---|
| 5,814,038 A | 9/1998 | Jensen et al. |
| 5,855,583 A | 1/1999 | Wang et al. |
| 6,007,550 A | 12/1999 | Wang et al. |
| 6,063,095 A | 5/2000 | Wang et al. |
| 6,080,181 A | 6/2000 | Jensen et al. |
| 6,096,004 A | 8/2000 | Meglan et al. |
| 6,132,368 A | 10/2000 | Cooper |
| 6,171,234 B1 | 1/2001 | White et al. |
| 6,171,277 B1 | 1/2001 | Ponzi |
| 6,346,072 B1 | 2/2002 | Cooper |
| 6,398,755 B1 | 6/2002 | Belef et al. |
| 6,413,264 B1 | 7/2002 | Jensen et al. |
| 6,445,984 B1 | 9/2002 | Kellogg |
| 6,461,372 B1 | 10/2002 | Jensen et al. |
| 6,527,782 B2 | 3/2003 | Hogg et al. |
| 6,620,174 B2 | 9/2003 | Jensen et al. |
| 6,726,675 B1 | 4/2004 | Beyar |
| 6,788,999 B2 | 9/2004 | Green |
| 6,850,817 B1 | 2/2005 | Green |
| 6,963,792 B1 | 11/2005 | Green |
| 6,974,465 B2 | 12/2005 | Belef et al. |
| 6,999,852 B2 | 2/2006 | Green |
| 7,006,895 B2 | 2/2006 | Green |
| 7,090,683 B2 | 8/2006 | Brock et al. |
| 7,118,582 B1 | 10/2006 | Wang et al. |
| 7,169,141 B2 | 1/2007 | Brock et al. |
| 7,204,844 B2 | 4/2007 | Jensen et al. |
| 7,214,230 B2 | 5/2007 | Brock et al. |
| 7,276,044 B2 | 10/2007 | Ferry et al. |
| 7,314,230 B2 | 1/2008 | Kumagai et al. |
| 7,331,967 B2 | 2/2008 | Lee et al. |
| 7,357,774 B2 | 4/2008 | Cooper |
| 7,371,210 B2 | 5/2008 | Brock et al. |
| 7,377,906 B2 | 5/2008 | Selkee |
| 7,537,570 B2 | 5/2009 | Kastelein |
| 7,630,752 B2 | 12/2009 | Viswanathan |
| 7,648,513 B2 | 1/2010 | Green et al. |
| 7,758,564 B2 | 7/2010 | Long et al. |
| 8,046,049 B2 | 10/2011 | Govari et al. |
| 2001/0053879 A1 | 12/2001 | Mills et al. |
| 2002/0042620 A1 | 4/2002 | Julian et al. |
| 2002/0072704 A1 | 6/2002 | Mansouri-Ruiz |
| 2002/0120254 A1 | 8/2002 | Julian et al. |
| 2002/0177789 A1 | 11/2002 | Ferry et al. |
| 2002/0183723 A1 | 12/2002 | Belef et al. |
| 2004/0077942 A1 | 4/2004 | Hall et al. |
| 2004/0254566 A1 | 12/2004 | Plicchi et al. |
| 2005/0038412 A1 | 2/2005 | Rabiner et al. |
| 2005/0065435 A1 | 3/2005 | Rauch et al. |
| 2005/0113719 A1 | 5/2005 | Saadat |
| 2005/0203382 A1 | 9/2005 | Govari et al. |
| 2005/0222554 A1 | 10/2005 | Wallace et al. |
| 2005/0228440 A1 | 10/2005 | Brock et al. |
| 2005/0277874 A1 | 12/2005 | Selkee |
| 2005/0283140 A1 | 12/2005 | Jensen et al. |
| 2006/0009735 A1 | 1/2006 | Viswanathan et al. |
| 2006/0041181 A1 | 2/2006 | Viswanathan et al. |
| 2006/0084911 A1 | 4/2006 | Belef et al. |
| 2006/0084945 A1 | 4/2006 | Moll et al. |
| 2006/0095022 A1 | 5/2006 | Moll et al. |
| 2006/0161136 A1 | 7/2006 | Anderson et al. |
| 2006/0161137 A1 | 7/2006 | Orban et al. |
| 2006/0161138 A1 | 7/2006 | Orban et al. |
| 2006/0167441 A1 | 7/2006 | Wang et al. |
| 2006/0229587 A1 | 10/2006 | Beyar |
| 2006/0235436 A1 | 10/2006 | Anderson et al. |
| 2006/0270915 A1 | 11/2006 | Ritter et al. |
| 2006/0293643 A1 | 12/2006 | Wallace et al. |
| 2007/0012135 A1 | 1/2007 | Tierney et al. |
| 2007/0019330 A1 | 1/2007 | Wolfersberger |
| 2007/0021776 A1 | 1/2007 | Jensen et al. |
| 2007/0043338 A1 | 2/2007 | Moll et al. |
| 2007/0043455 A1 | 2/2007 | Viswanathan et al. |
| 2007/0149946 A1 | 6/2007 | Viswanathan et al. |
| 2007/0233044 A1 | 10/2007 | Wallace et al. |
| 2007/0239172 A1 | 10/2007 | Lee et al. |
| 2007/0250073 A1 | 10/2007 | Brock et al. |
| 2007/0250074 A1 | 10/2007 | Brock et al. |
| 2007/0260115 A1 | 11/2007 | Brock et al. |
| 2007/0276423 A1 | 11/2007 | Green |
| 2007/0283263 A1 | 12/2007 | Zawde et al. |
| 2007/0299479 A1 | 12/2007 | Saksena |
| 2008/0009791 A1* | 1/2008 | Cohen et al. ............... 604/95.01 |
| 2008/0039869 A1 | 2/2008 | Mills et al. |
| 2008/0045892 A1 | 2/2008 | Ferry et al. |
| 2008/0059598 A1 | 3/2008 | Garibaldi et al. |
| 2008/0119824 A1 | 5/2008 | Weitzner et al. |
| 2008/0119872 A1 | 5/2008 | Brock et al. |
| 2008/0125793 A1 | 5/2008 | Brock et al. |
| 2008/0125794 A1 | 5/2008 | Brock et al. |
| 2008/0140087 A1 | 6/2008 | Barbagli |
| 2008/0147091 A1 | 6/2008 | Cooper |
| 2008/0215065 A1 | 9/2008 | Wang et al. |
| 2008/0245946 A1 | 10/2008 | Yu |
| 2008/0249536 A1 | 10/2008 | Stahler et al. |
| 2008/0300574 A1* | 12/2008 | Belson et al. ................ 604/510 |
| 2008/0300592 A1 | 12/2008 | Weitzner et al. |
| 2009/0012533 A1 | 1/2009 | Barbagli et al. |
| 2009/0082722 A1 | 3/2009 | Munger et al. |
| 2009/0105639 A1 | 4/2009 | Weitzner et al. |
| 2009/0105645 A1 | 4/2009 | Kidd et al. |
| 2009/0248043 A1 | 10/2009 | Tierney et al. |
| 2010/0168735 A1* | 7/2010 | Deno ..................... A61B 5/053 606/34 |
| 2011/0105954 A1* | 5/2011 | Cohen et al. ................. 600/585 |
| 2012/0209174 A1* | 8/2012 | Moll et al. ................. 604/95.01 |
| 2012/0220931 A1 | 8/2012 | Cohen et al. |

OTHER PUBLICATIONS

State Intellectual Property Office of the People's Republic of China, First Office Action, Oct. 30, 2009, Chinese Patent Application 200680025512.7, "Remotely Controlled Catheter Insertion System," with English translation, (24 pgs. total).

International Preliminary Report on Patentability, Intl Application PCT/US2009/031357. International Bureau of WIPO, Jul. 29, 2010.

International Search Report and Written Opinion, Intl Application PCT/US2009/031357. International Search Authority, U.S. Patent and Trademark Office (ISA/US), Mar. 19, 2009.

U.S. Appl. No. 13/051,736, Final Office Action dated Nov. 5, 2012.

Hein et al., "Robot Supported Insertion of Catheters for Hyperthermia and Branch Therapy," Computer Assisted Radiology and Surgery, 1998, pp. 660-663.

Macoviak, "Catheter System for Surgical Access and Circulatory Support of the Heart," USPTO, Official Gazette, vol. 1278, Jan. 6, 2004.

U.S. Appl. No. 13/051,736, Non-Final Office Action dated Jul. 17, 2012.

U.S. Appl. No. 12/903,397, Non-Final Office Action dated Nov. 19, 2012.

Canadian Application 2,646,846, Office Action dated Sep. 19, 2012.

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

* cited by examiner

COMPONENTS AND METHODS FOR ACCOMMODATING GUIDEWIRE CATHETERS ON A CATHETER CONTROLLER SYSTEM

BACKGROUND

Many invasive medical procedures require the use of radiation to visualize and track the location of an inserted device. For example, procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system.

High dosages of radiation may have long term adverse health effects. A patient may be directly exposed only once or twice to radiation during such procedures and avoid such adverse effects. However, physicians, medical technicians and staff can experience a large cumulative radiation dosage over time, both directly and indirectly, from conducting many procedures even.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury.

SUMMARY OF THE INVENTION

Various embodiments provide systems and methods for controlling a catheter with a catheter positioning device by using a remote controller, thereby helping to reduce exposure to radiation of physicians, medical technicians and staff involved in catheter procedures. The embodiment systems for remotely controlling a catheter enable use of a guidewire to help position the catheter. In various embodiments, a catheter positioning device may include a guidewire control mechanism that may be used to draw a guidewire through a catheter coupled with the catheter positioning system. As the catheter is advanced over the guidewire by the catheter positioning device, the guidewire control mechanism may draw the guidewire away, such as collecting any slack on the guidewire. In further embodiments, the guidewire control mechanism may match the speed at which the guidewire is drawn to the speed at which the catheter advances, thereby maintaining the position of the guidewire relative to the patient (i.e., the tip of the guidewire may remain in place at a desired operation site inside the patient as the catheter advances). In further embodiments, the guidewire control mechanism may also collect the guidewire after it is drawn through the catheter, such as on one or more spools, rollers, or pulleys, and may be used to remove the guidewire from the patient after the catheter is in position.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

A guidewire may be used to help position many types of catheters within a patient. A guidewire is typically a wire that is thinner than the catheter desired for an operation, and therefore may be easier to insert and position within a patient. Also, a guide wire may be easier to image using fluoroscopy than a catheter, and thus may be easier for the physician to observe with imaging systems during the insertion procedure. Once the guidewire is in place, the catheter may be advanced over the guidewire to reach the site of the operation.

Various embodiments provide systems and methods for controlling a catheter with a catheter positioning device by using a remote controller that accommodates a guide wire as commonly used with many types of catheters. The embodiment systems for remotely controlling a catheter allow a physician to remotely control a catheter away from any sources of radiation used for imaging or other procedures and thereby avoid harm associated with repeated exposure to radiation or caused by heavy protective gear. A catheter may include a proximal portion or handle that may be fitted or attached to the catheter positioning device. The catheter positioning device may then be used to move the attached catheter, such as advancing or retracting the catheter in relation to a patient or within a patient's body. The catheter positioning device may also be used to actuate the catheter, such as by controlling an actuator on a catheter's handle. Catheter actuators may perform various tasks, such as deflecting a tip to help in navigation or controlling one or more transducers to assist in an operation.

In various embodiments, a catheter positioning device may include a guidewire control mechanism that may be used to draw a guidewire through a catheter coupled with the catheter positioning system. As the catheter is advanced over the guidewire by the catheter positioning device, the guidewire control mechanism may draw the guidewire away, such as to collect any slack in the guidewire. In further embodiments, the guidewire control mechanism may match the speed at which the guidewire is drawn to the speed at which the catheter advances and thereby maintain the position of the guidewire relative to the patient. In this manner, the tip of the guidewire may remain in place at a desired operation site inside the patient as the catheter advances. In further embodiments, the guidewire control mechanism may also collect the guidewire after it is drawn through the catheter, such as on one or more spools, rollers, or pulleys, and may be used to remove the guidewire from the patient after the catheter is in position.

Figure 1:
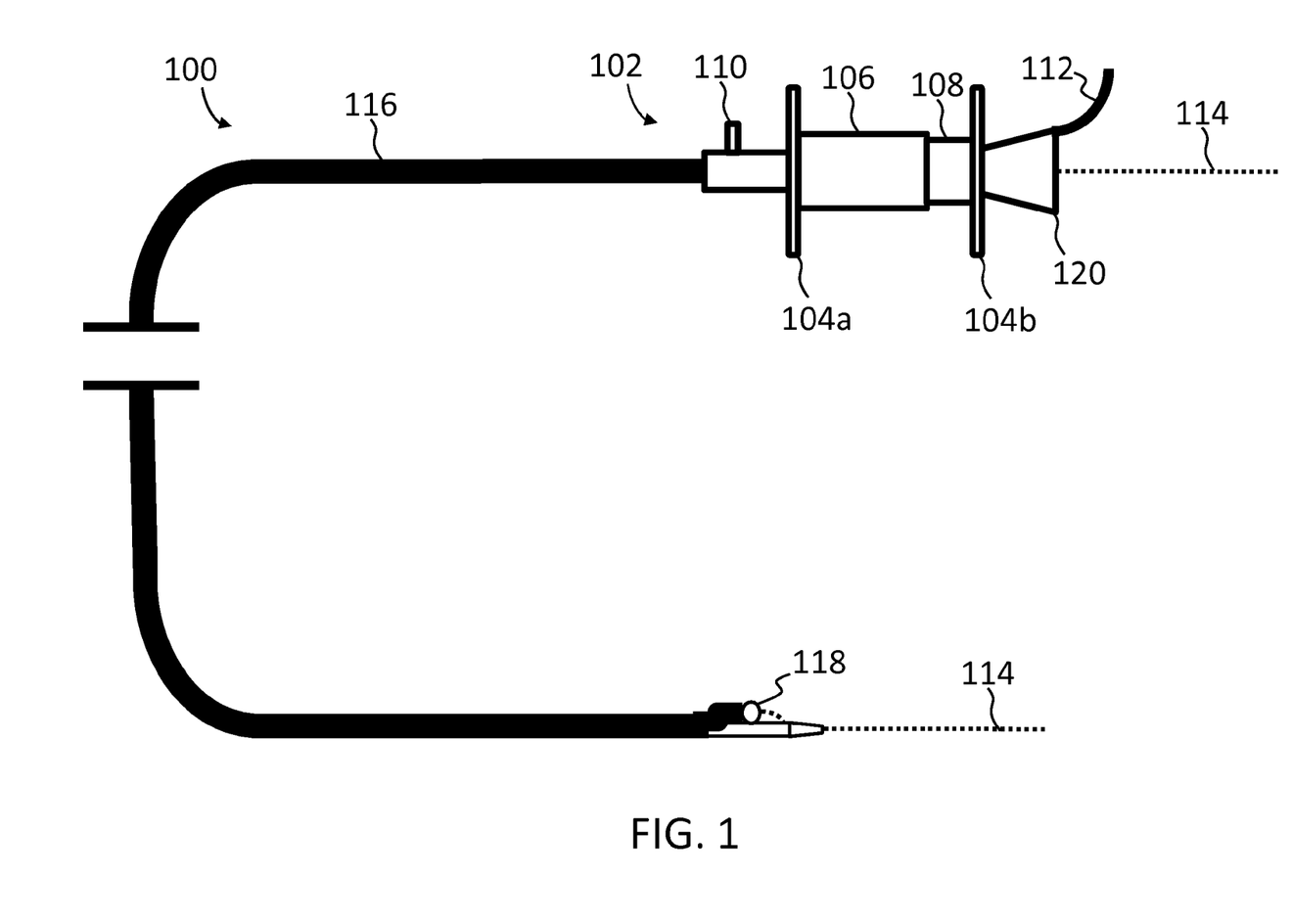
FIG. 1 is a top view of a catheter which could be used in accordance with various embodiments.

FIG. 1 illustrates an example catheter 100 that may be used in various embodiments. The catheter 100 may include a handle portion 102 and tube portion 116. The handle portion 102 may be located at a proximal end of the catheter 100 while the distal end of the tube portion 116 may be inserted into the body of a patient.

The handle portion 102 of the catheter 100 may also include an irrigation port 110, which may be used to introduce water or other fluids to lubricate the catheter and ease insertion or retraction into the patient. The handle portion 102 may also include a back port 120 through which one or more wires or cables 112 may leave the handle portion 102. For example, as shown in FIG. 1, the catheter 100 may have a guidewire 114 that runs inside the length of the catheter exiting out the proximal end of the tube portion 116 and out the back port 120. In further embodiments, cables 112 may supply power to the catheter 100 or transmit signals, such as sending commands from a remote controller or other control device to the catheter or relaying data from one or more transducers present on the catheter.

The handle portion 102 may include actuators to control the behavior of the catheter 100. For example, the handle portion 102 shown in FIG. 1 includes a front flange 104a and rear flange 104b that may be squeezed together such that the inner cylinder 108 slides inside the outer cylinder 106. This motion may actuate one or more mechanism at the tip of the catheter, such as extending a laser tip 118 from inside the tube portion 116 of the catheter 100. The laser tip 118 may be retracted by pulling the front flange 104a and rear flange 104b apart.

If the catheter has a guidewire 114 running through it as shown in FIG. 1, the laser tip 118 may also have the guidewire 114 extend through it such that extending the laser tip 118 includes moving the laser tip 118 away from the catheter's longitudinal axis (e.g., outside of a sheath or along a curved guide near the end of the catheter). The guidewire 114 may run out of the laser tip 118 back into the catheter and out the end of the catheter 100.

One or more cables 112 connected to the catheter 100 may provide power or control whether and what power level the laser tip 118 is active. In various embodiments, one or more cables 112 may be a fiber optic feed to a laser tip 118. In further embodiments, the catheter positioning device may rotate or move the catheter while the laser tip 118 is active in order to apply the laser to tissue in an arc, such as around the perimeter of a blood vessel, rather than simply directing the laser at a single site forward.

In alternate embodiments, various other catheters may be used with different actuators or functions, such as actuators for deflecting the tip of the catheter to ease navigation inside a patient or for controlling one or more transducers at the tip (e.g., electrical leads, one or more sensor devices, ultrasound devices, etc.).

Figure 2:
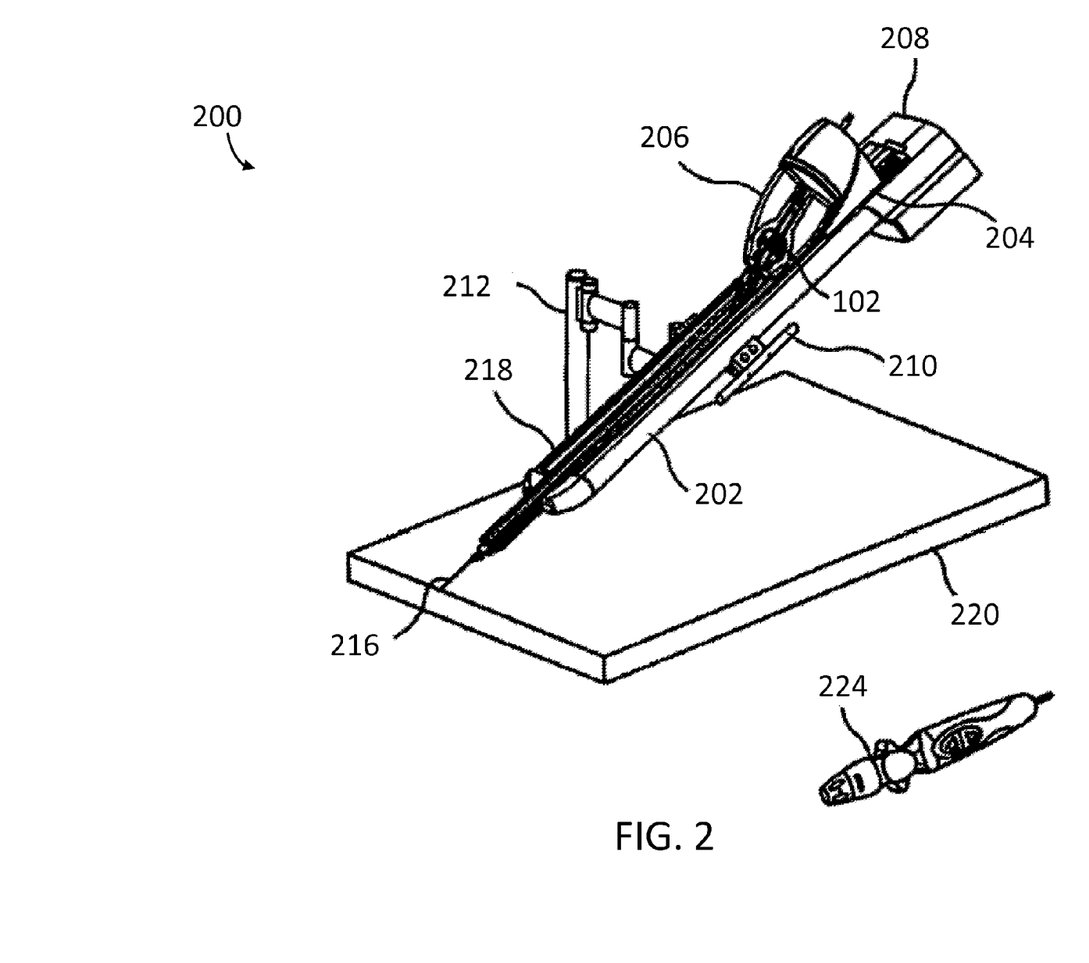
FIG. 2 is an oblique view of a remotely controlled catheter positioning device in accordance with various embodiments.

FIG. 2 illustrates an embodiment catheter positioning device 200 with a remote controller 224. The catheter positioning device 200 may include a sled base 202 coupled with a sled member 204. The sled base 202 may be configured to advance the sled member 204 along the sled base 202 towards the body of the patient or back away from the patient. For example, the sled member may be moved with a motor 208 at one end of the sled base 202. The sled member 204 may move along a rail or other track, such as a worm drive, back and forth along the longitudinal axis of the sled base 202.

The sled base may be mounted with an arm 212, such as over an operating table 220. The arm 212 may be extended or rotated to position the sled base 202 relative to a patient on the operating table 220. The sled base 202 may include a handle 210 to move the sled base 202 into position. The sled base may also include a nose cone 216 that may be inserted into a patient. Alternately, the nose cone 216 may connect with an introducer or sheath that may be inserted into the patient. A catheter may be advanced along the sled base 202 and then through the nose cone 216 into the patient.

The sled base 202 may include a sterile barrier to protect the catheter. In various embodiments, the sterile barrier may include a resealable delivery channel 218 configured to receive and guide the catheter along the sled base as it is advanced by the sled member 204. For example, the catheter may be inserted into the delivery channel 218 and then the catheter handle 102 may be connected to the sled member 204 (such as by using the modular plate 206 discussed below) such that the catheter is driven forward by translation of the sled member 204 along the resealable delivery channel 218 in the sled base 202 and through the nose cone 216 into the patient.

The resealable delivery channel 218 may be flexible to allow the catheter to be inserted and removed repeatedly. For example, the resealable delivery channel may have a resealing groove with flexible plastic lips running along the top of the delivery channel along the longitudinal axis of the sled base 202. The catheter may be pushed through the resealing groove to get inside the resealable delivery channel 218 (i.e., the plastic lips may separate to let the catheter pass then come back together to seal behind the catheter). The catheter may be removed by pulling the catheter back through the flexible plastic lips of the resealing groove.

The sled member 204 may be coupled with a modular plate 206 to which a catheter handle 102 may be attached. Various embodiments may include many alternate modular plates 206 that may be swapped out so that the catheter positioning system may be used with many different types of catheters. Depending on what kind of catheter is desired for a procedure, an appropriate modular plate 206 may be attached to the sled member 204 and the catheter may be attached to the module plate 206. The modular plate 206 may also integrate with any actuators on the catheter handle 102 thereby allowing an operator to control the actuators via the remote controller 224.

The sled member 204 may rotate, thereby rotating a catheter connected to the modular plate 206. This rotation may be controlled remotely via the remote controller 224. By controlling translation along the sled base 202, rotation of the sled member 204, and actuation of the catheter's handle via the modular plate 206, an operator may position or use the catheter in any way necessary for a desired operation. Further, an operator may control each of these degrees of freedom (i.e., translation, rotation, actuation) remotely with the remote controller 224.

Figure 3:
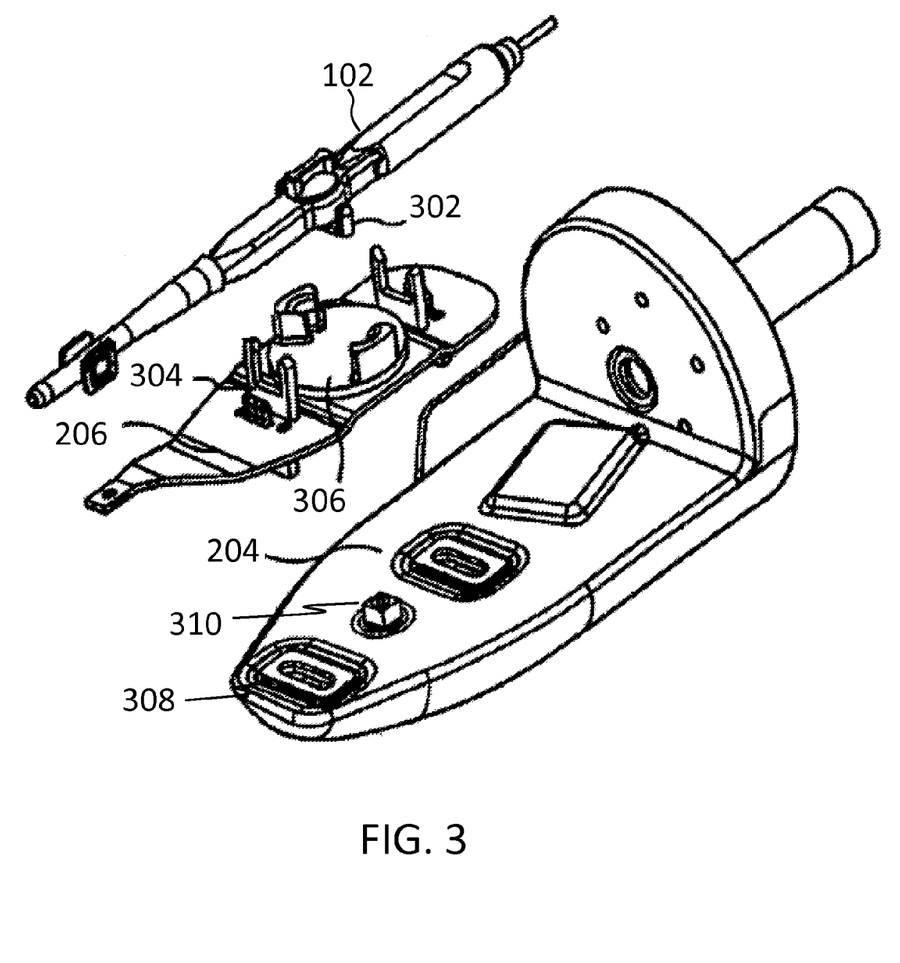
FIG. 3 is an exploded view of a catheter handle portion, a modular plate, and a sled member according to various embodiments.

FIG. 3 illustrates an exploded view of a catheter handle 102, modular plate 206, and sled member 204. The catheter handle 102 may include one or more actuators 302. FIG. 3 illustrates a catheter handle 102 with a rotatable lever as opposed to the flanges 104a and 104b shown in FIG. 1. As discussed above, the modular plate 206 may be swapped out so that various catheters with different actuators may be connected to the catheter positioning device. FIG. 3 illustrates a modular plate 206 that includes clamps 304 to secure the catheter handle 102 as well as a molded nest 306 configured to integrate with the actuator 302 (i.e., the rotatable lever may be controlled by rotating the molded nest 306).

The modular plate 206 may be rigidly connected to the sled member 204 such that translation or rotation of the sled member is transferred through the modular plate 204 to the catheter handle 102 to drive and position the catheter. The sled member 204 and modular plate 206 may be connected by one or more detachable joints 308, such as a socket that part of the modular plate 204 may plug into. The sled member 204 may also include a control mechanism 310 to integrate with the modular plate 206. The control mechanism 310 may allow the operator to control the catheter's actuators 302, such as by controlling the molded nest 306. The control mechanism 310 may be configured to integrate with any of the various modular plates 204 designed to connect with different catheter handles. In various embodiments, the control mechanism 310 may be a simple element (such as a rotational element shown in FIG. 3) that can drive one or more catheter specific control devices of the modular plate (e.g., driving the molded nest 304 configured for a particular type of catheter handle 102).

Figure 4:
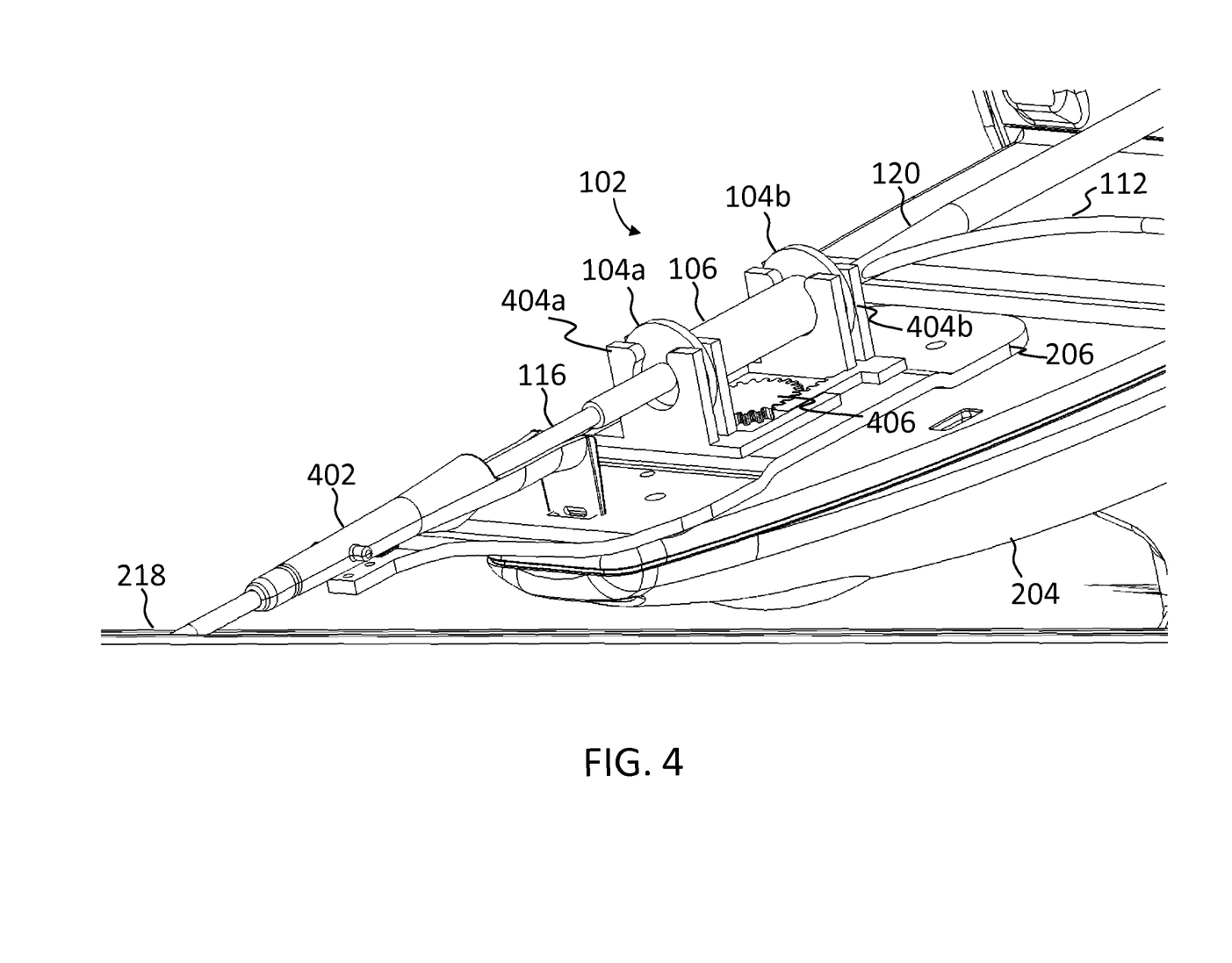
FIG. 4 is an oblique view of a catheter handle portion, a modular plate, and a sled member coupled together according to various embodiments.

FIG. 4 illustrates an example embodiment in which the catheter of FIG. 1 may be connected with the modular plate 206 and sled member 204. The modular plate 206 may include clamps 404a and 404b for securing the catheter handle's flanges 104a and 104b. The modular plate 206 may also include a gear 406 that may rotate to move the clamps 404a and 404b. As shown in FIG. 4, the gear 406 may have teeth that mesh with teeth on an arm extending from one or both clamps 404a and 404b such that rotation of the gear 406 is converted into translation of one or both clamps 404a and 404b. The gear 406 may be controlled from underneath by a control mechanism 310 (not visible in FIG. 4) on the sled member 204 that may be rotated based on commands from the remote controller.

By moving the clamps 404a and 404b, the catheter handle 102 may be actuated, such as squeezing the flanges 104a and 104b together to drive inner cylinder 108 (not visible in FIG. 4) into outer cylinder 106 and thereby extend a laser tip 118 (not shown in FIG. 4).

The modular plate 206 may be attached to an introducer 402, which may lead the catheter's tube portion 116 into the resealable delivery channel 218. As the sled member 204 is advanced, the end of the introducer 402 may stay inside the resealable delivery channel 218 by moving between the plastic lips of the resealable groove.

The catheter handle 102 may include a back port 120 which may have one or more cables or tubes 112 that are led back, such as through the sled member 204.

Figure 5:
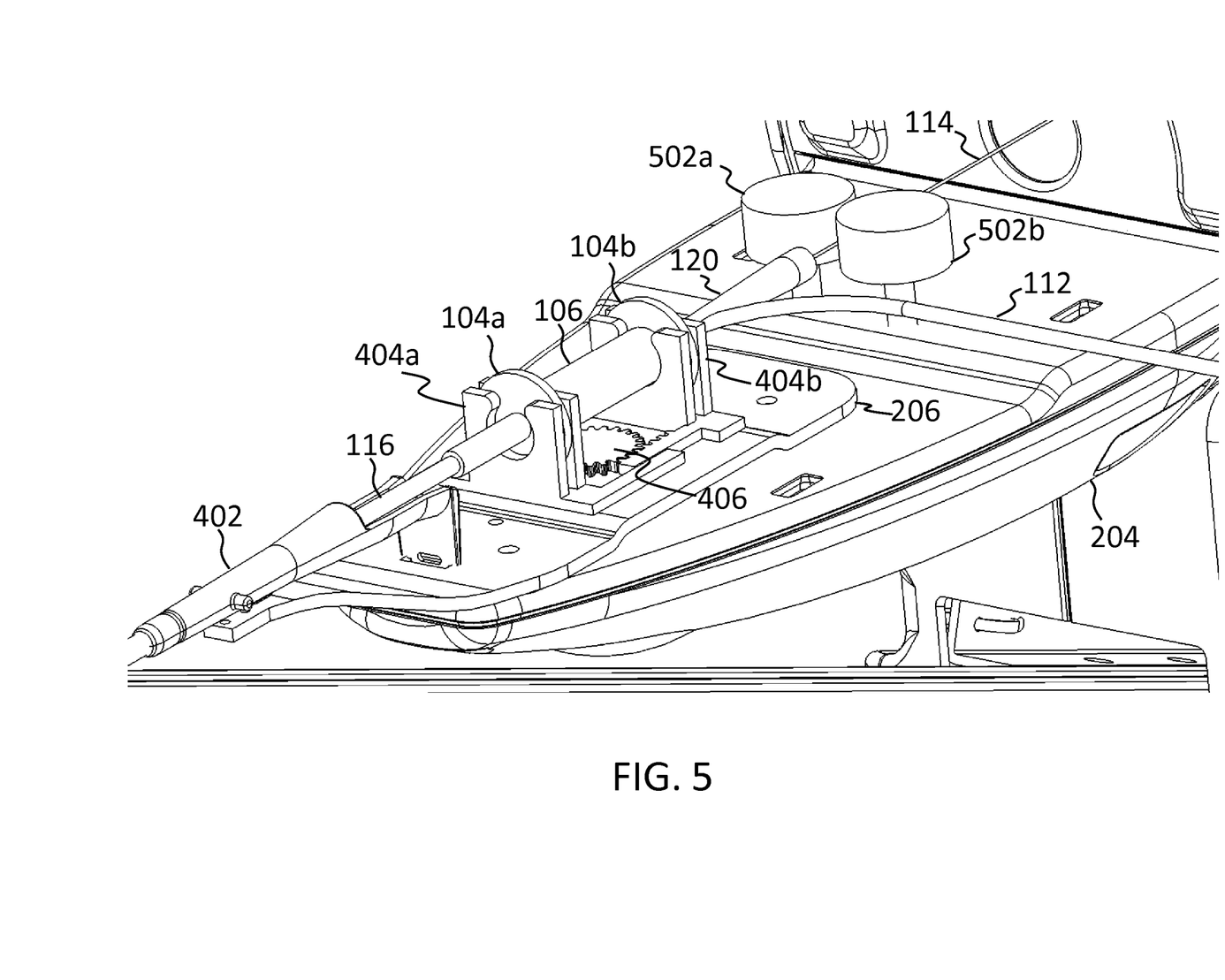
FIG. 5 is an oblique view of a sled member with rollers acting as a guidewire control mechanism according to various embodiments.

FIG. 5 illustrates an example embodiment with a catheter attached to a modular plate 206 and sled member 204. The sled member 204 may include a guidewire control mechanism, illustrated in FIG. 5 as a pair of rollers 502a and 502b, that acts to draw a guidewire 114 through the catheter and away from the body of the patient. The guidewire 114 may extend through the catheter and exit through the back port 120 where the guidewire 114 is engaged by the rollers 502a and 502b. The rollers 502a and 502b may press on opposite sides of the guidewire 114 and rotate about their vertical axes in alternate directions (e.g., the first roller 502a may rotate counterclockwise and the second roller 502b may rotate clockwise or vice versa) to draw the guidewire 114.

The speed of drawing the guidewire may be controlled by adjusting the rate of rotation of the rollers 502a and 502b. In various embodiments, the speed of drawing the guidewire 114 may be matched to the speed of advancement of the sled member 204 so that the catheter advances over the guidewire 114 while the guidewire remains stationary relative to the patient. This is further illustrated in FIGS. 7A-7C and discussed below.

Figure 6:
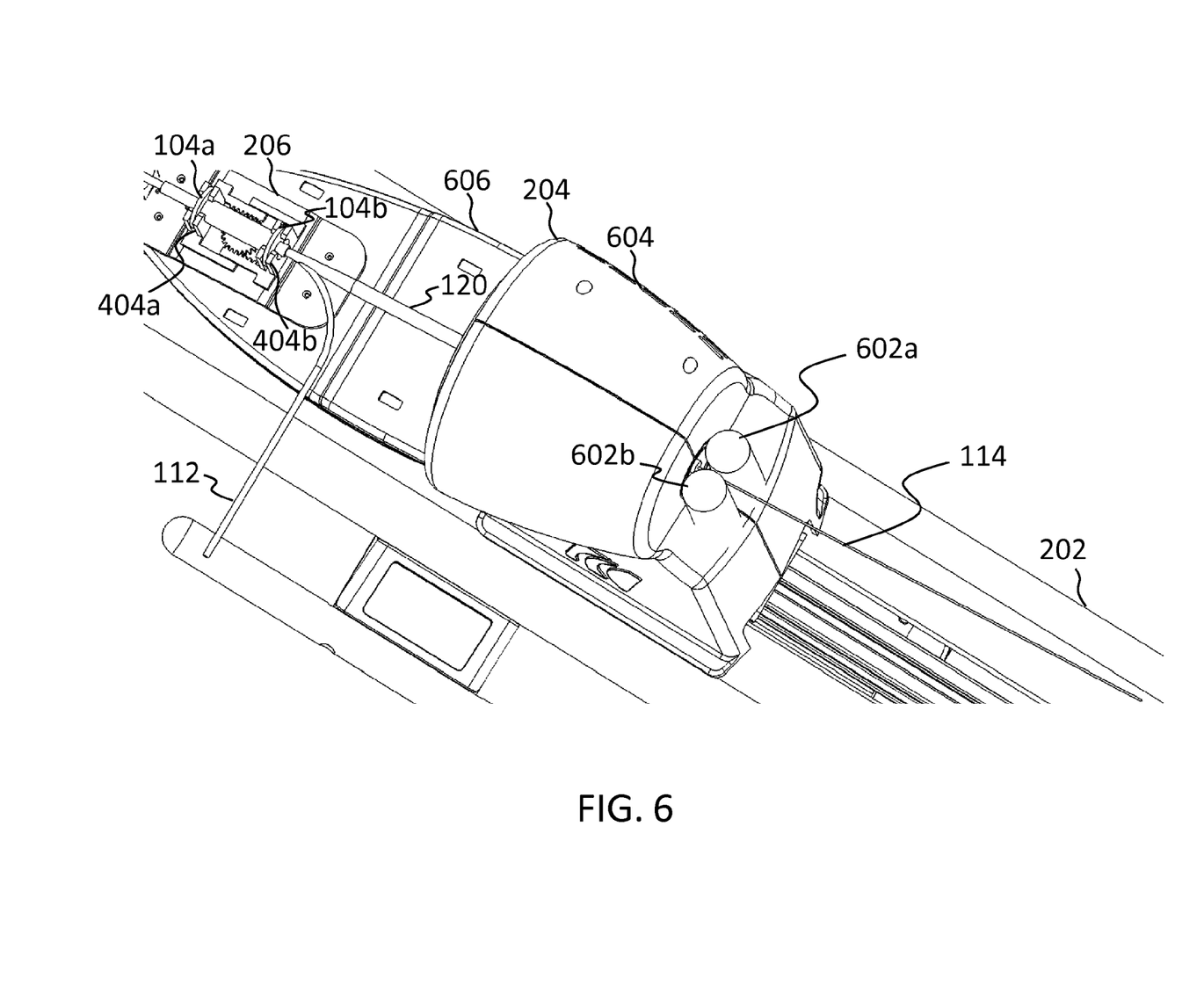
FIG. 6 an oblique view of a sled member with rollers on the back of the sled member acting as a guidewire control mechanism according to various alternate embodiments.

FIG. 6 illustrates an alternate embodiment with rollers 602a and 602b positioned on the back of the sled member 204. A guidewire 114 may extend from the catheter's back port 120 and through a hole or port in a turret portion 604 of the sled member 204. This turret portion 604 may include a motor (not visible) to rotate the remaining integration portion 606 (i.e., the portion that integrates with the modular plate 206 and catheter handle 102). The integration portion 606 may be rotated to rotate the catheter while the guidewire 114 continues to pass through the turret portion 604 (which may not rotate) and on to the rollers 602a and 602b which draw the guidewire 114 back by rotating as described above.

Figure 7A:
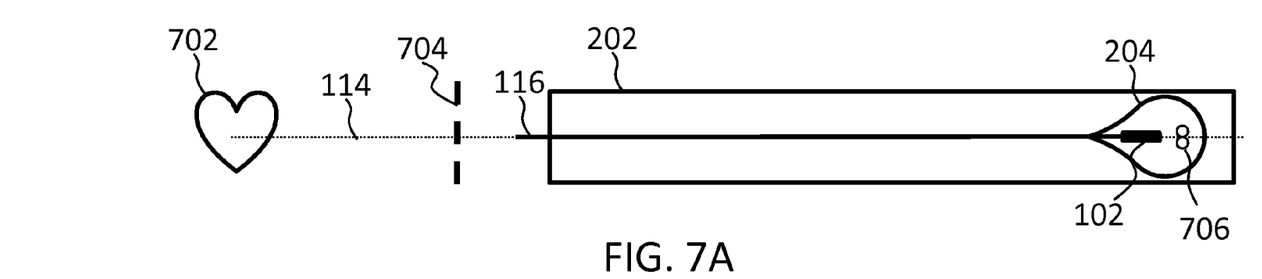
FIGS. 7A-7C are a sequence of diagrams showing the progress of a catheter as it is advanced over a guidewire according to various embodiments.
Figure 7B:
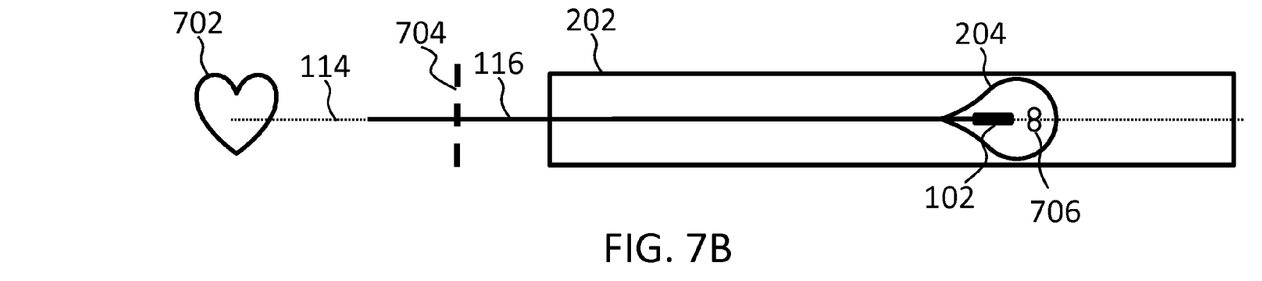
Figure 7C:
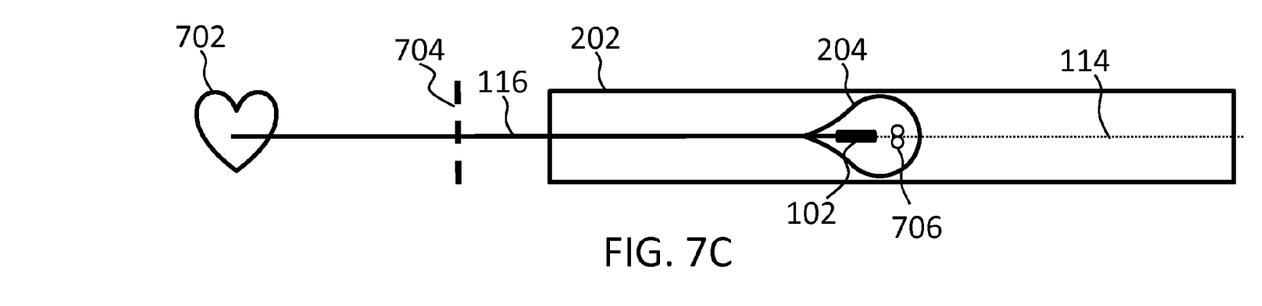

FIGS. 7A-7C illustrate sequential steps as a catheter is advanced over a guidewire 114. Initially, in FIG. 7A, the guidewire 114 may be positioned with one end at a desired location 702 for a catheter procedure, such as in a patient's heart. The other end of the guidewire may be run outside of the patient (the boundary 704 of the patient's body is illustrated as a dotted line) through a catheter's tube portion 116 and handle portion 102 and back to a guidewire control mechanism 706 on the sled member 204. The positioning of the guidewire within the patient may be accomplished using conventional procedures, or using the catheter positioning device as described below. The catheter may be loaded into the catheter positioning system with the tube portion 116 running along the sled base 202, such as in a resealable delivery channel (not shown), and with the catheter handle 102 attached to the sled member 204, such as with a modular plate 206 (not shown).

In various embodiments, the guidewire 114 may be advanced into the patient to the desired location by using the catheter positioning device, thereby allowing an operator to remotely control the guidewire while using radioactive imaging to observe the guidewire's progress. The radioactive imaging may be terminated and a catheter may then be advanced over part of the guidewire and loaded into the catheter positioning device. The operator may then remotely control the catheter positioning system to advance the catheter over the guidewire into the patient while using radioactive imaging again.

FIG. 7B illustrates how a catheter may be driven by translation of the sled member 204 along the sled base 202. The catheter's handle portion 102 may travel with the sled member 204 while the catheter's tube portion 116 may advance over the guidewire, such as through a nose cone and into the patient.

The guidewire control mechanism 706 may draw the guidewire back as the catheter is advanced. If the guidewire 114 is drawn back at the same speed as the catheter is advanced (i.e., the same speed as the translation of the sled member 204), then the guidewire may remain stationary in relation to the patient. As shown in FIG. 7B, the end of the guidewire may remain in the same desired location 702 in the patient.

FIG. 7C illustrates the catheter fully advanced along the guidewire 114 to the desired location 702 in the patient. The guidewire 114 may be removed from the catheter. If the sled member 202 remains stationary, the guidewire control mechanism 706 may draw the guidewire completely out of the catheter (or the guidewire may be drawn manually since the radioactive imaging may be stopped once the catheter is in place). Removal of the guidewire 114 may allow one or more other devices or objects to travel down the catheter. Once fully advanced, the catheter may be operated at the desired location 702, such as actuating the catheter handle to extend a laser tip and activating the laser tip on a particular tissue within the patient.

In alternate embodiments, the guidewire control mechanism 706 (e.g., the rollers 502a and 502b) may be used to advance the guidewire through the catheter. For example, the rollers 502a and 502b may be rotated in the opposite direction to push the guidewire 114. If a catheter is already loaded in the catheter positioning device, the guidewire control mechanism may be used to advance a guidewire through the catheter and then into position within a patient. In alternate embodiments, the catheter positioning device may alternate advancing the catheter and the guidewire in a series of steps.

In alternate embodiments, the guidewire control mechanism 706 may not advance the guidewire 114 (i.e., remain stationary) such that the guidewire 114 moves with the catheter. For example, the catheter and guidewire 114 may be advanced together to get into position prior to an operation and then the guidewire control mechanism 706 may be activated to advance the catheter over the guidewire 114 without moving the guidewire 114 relative to the patient.

Figure 8:
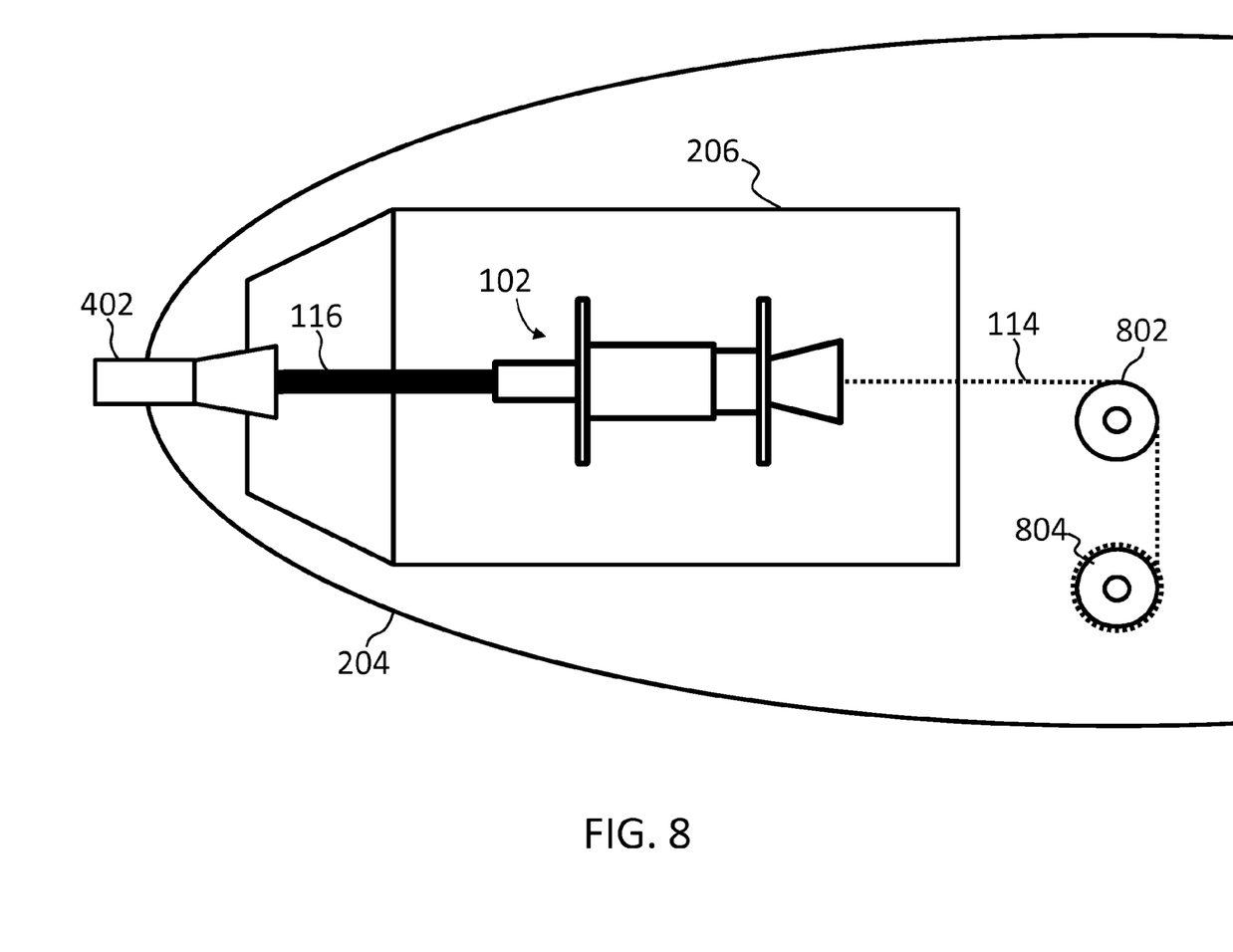
FIG. 8 is a diagram of a catheter handle portion, a modular plate, and a sled member coupled together wherein the sled member comprises a guidewire control mechanism including a pulley and a spool according to various embodiments.

FIG. 8 illustrates an alternate guidewire control mechanism on the sled member 204. As previously discussed, the catheter handle portion 102 may be connected to the modular plate 206 with the catheter tube portion being run through an introducer 402. The modular plate 206 may be attached to the sled member 204. A guidewire 114 may extend through the catheter and out the back of the catheter handle to the guidewire control mechanism, which may include a spool 804 to collect the guidewire as well as one or more pulleys 802 to redirect the guidewire onto the spool 804.

The spool 802 may be rotated about its vertical axis (i.e., the z axis or the axis coming out of the page of FIG. 8) and the guidewire may be drawn from the catheter and wrap around the spool 804. The spool 804 may include a connection point to initially secure the guidewire 114, and the guidewire 114 may be secured thereafter by tension from being wrapped around the spool.

One or more pulleys 802 may be used to direct the guidewire. For example, as a guidewire wraps around the spool 804, the effective radius of the spool may increase (due to the thickness of the guidewire wrapped around it) and the angle at which the spool 804 draws the guidewire may change with the effective radius. A pulley 802 may insure that the guidewire is pulled directly back at all times. Alternately, one or more pulleys may be used to direct the guidewire so that a spool or rollers may be located various other places, such as on or off the sled member 204.

The rotational speed of the spool 802 may be adjusted so that the speed of drawing the guidewire 114 matches the speed of catheter advancement (i.e., the speed of translation of the sled member 204). Therefore, the guidewire 114 may remain stationary relative to the patient and/or a desired location within the patient, similar to the motion described with regard to the rollers above.

Figure 9:
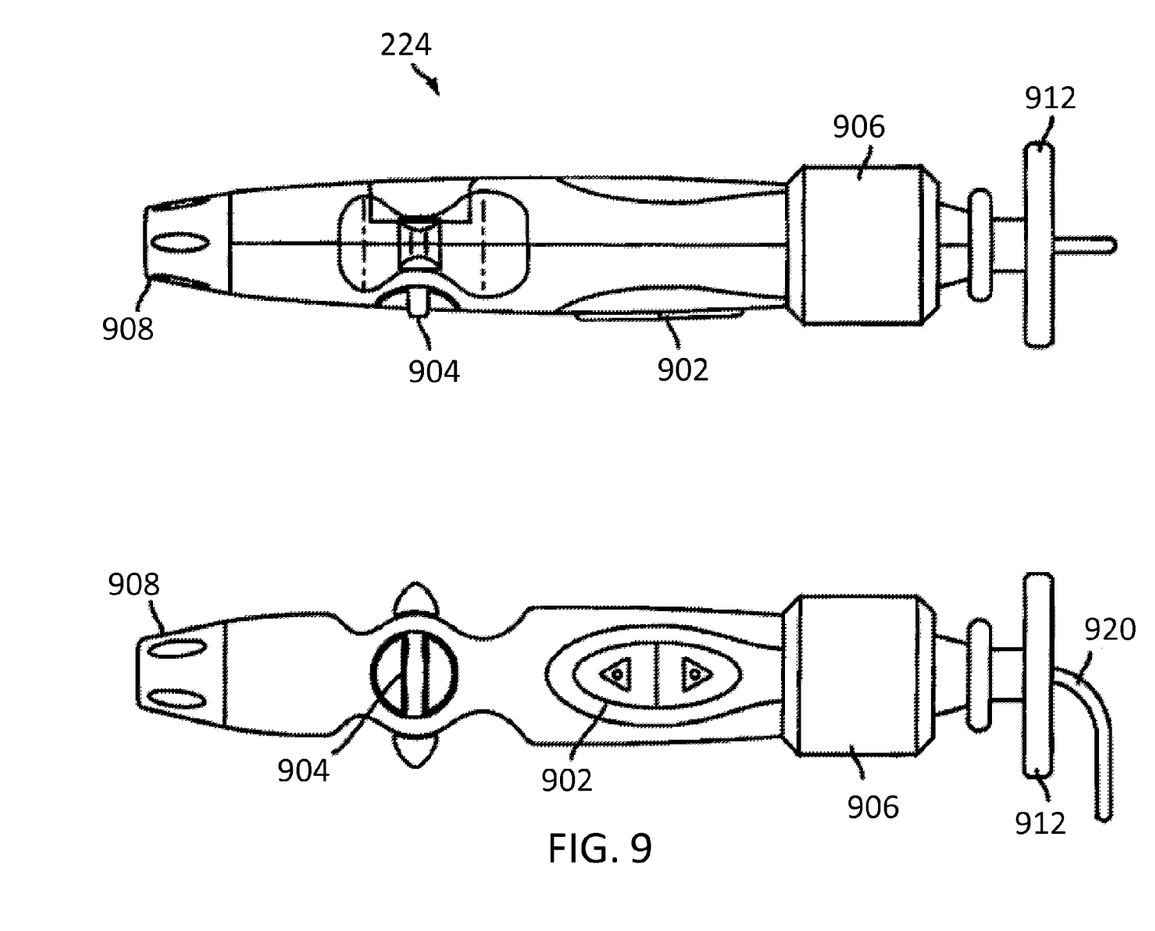
FIG. 9 is a top and side view of a remote controller in accordance with an embodiment of the invention.

FIG. 9 illustrates an embodiment remote controller 224 from a side and top perspective. The remote controller 224 may include buttons 902 for controlling the in and out or forward and backward motion of a catheter provided by sliding the sled member 204 up or down the sled base 202. The remote controller 224 may include a dial 908 at one end for controlling rotation of the catheter by rotating the sled member 204. Control signals may be sent from the remote controller 224 to the catheter positioning device via a wire 920 or wirelessly via a transmitter (not shown).

The remote controller 224 may also include a rotatable knob 904 that may send control signals to the sled member to control actuation of one or more actuators on the catheter handle 102. For example, rotation of rotatable knob 904 may correspond to rotation of the gear 406 to move the catheter handle's front flange 104a and rear flange 104b and extend the laser tip 118. In another example embodiment, rotation of the rotatable knob 904 may correspond to rotation of a molded nest on the modular plate to rotate a catheter handle's actuator and result in deflection of a distal tip of the catheter.

The remote controller 224 may also include a rotatable sleeve 906 that may be rotated to provide a user input. Rotation of this sleeve 906 may be may be transmitted to the sled member 178 to control a drive motor to control rotational motions applied to a rotatable sleeve or other actuator on the catheter handle 102. In example embodiment, rotation of the rotatable sleeve 906 may result in deflection of a distal tip of the catheter in a plane perpendicular to the plane of deflection of the distal tip controlled by the rotatable knob 904. Rotation of the rotatable sleeve 906 may alternatively be translated into other control actions, such as changing the size or shape of a distal portion of the catheter.

The remote controller may also include a push pull user input device 912 that may similarly be configured to control actuation of another catheter element. For example, in or out movement of the push pull user input device 912 may correspond to translational movements applied to a push pull actuator on the catheter handle 102. In an alternate example embodiment, pushing or pulling the push pull user input device 912 may result in changing the diameter of a loop (or other shape change feature) on the distal tip of the catheter.

Figure 10:
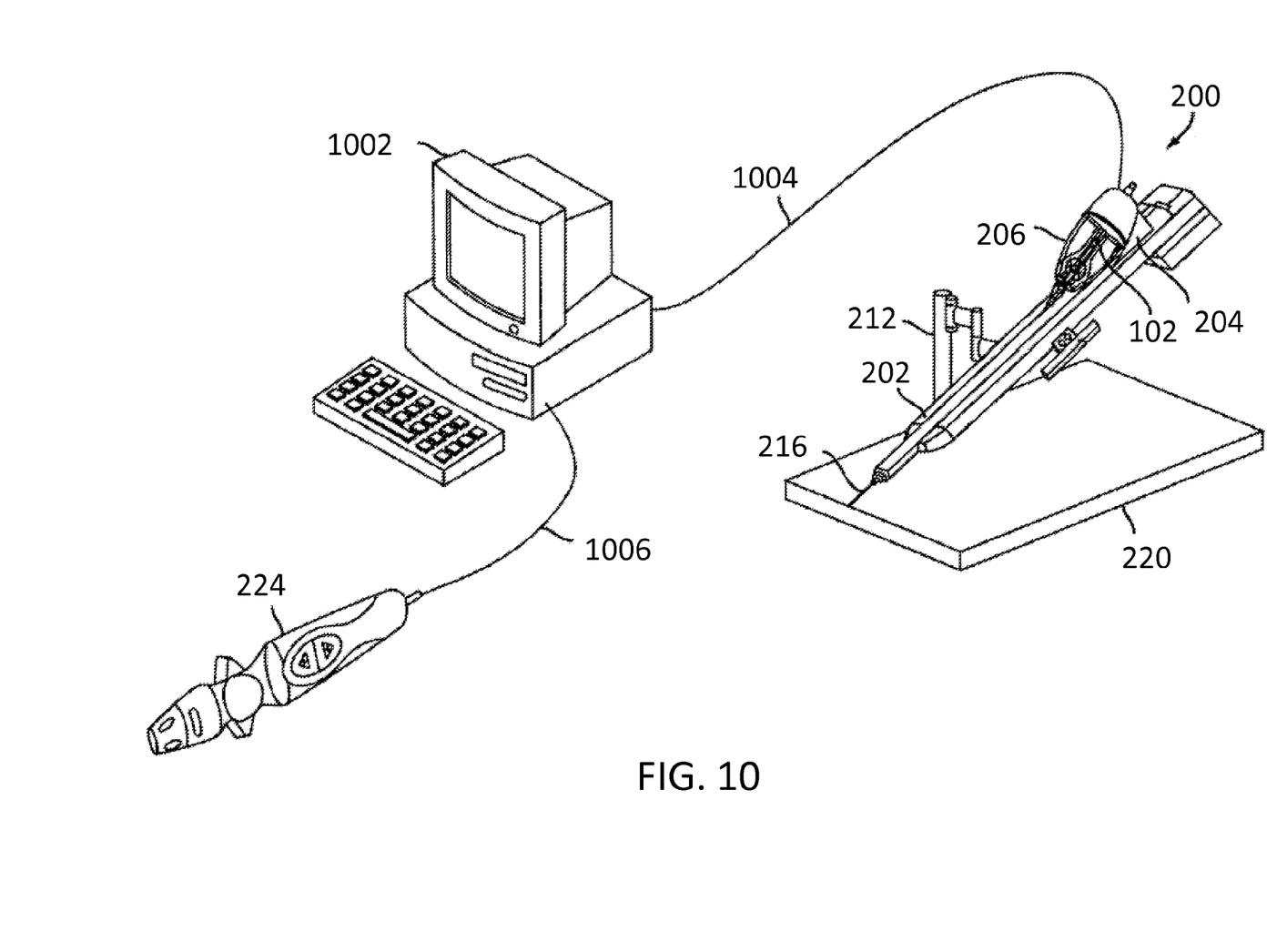
FIG. 10 is a system block diagram of a remote controller, a remotely controlled catheter system, and a programmable control system.

FIG. 10 illustrates a programmable control system 1002 as a part of the catheter positioning system. A remote controller 224 may be connected to the programmable control system 1002 by a wired connector 1006 or a wireless data link (not shown). The programmable control system 1002 may also be connected to the catheter positioning device 200 by a wired connector 1004 or a wireless data link (not shown).

The programmable control system 1002 may output command signals to the positioning device 200 based on training or programming, such as programmed movements for automatic positioning of the catheter and/or guidewire. Programmed movements of the positioning device may be input prior to a medical procedure, such as by entering commands into the programmable control system 1002 (e.g., via a keyboard) or by training the system, such as through manipulation of the remote controller. For example, a user may train the programmable control system to direct the positioning system to execute a series of translation and rotation movements by manipulating the control inputs on the controller as if directing the movements in real time. The programmable control system may store the command inputs and then combine the commands into a single programmed movement, such as in response to an operator selecting a number of pre-trained/programmed movements that should be accomplished in an indicated sequence. Programmed movements may include various combinations of the commands, such as simultaneously rotating and translating the system to create a "corkscrew" maneuver. These programmed movements may be triggered later by a single input, such as a user identifying the sequence by a file name or preset program and pressing an execute key on the controller or the system keyboard.

While preferred embodiments have been described, the invention is only limited by the scope of the claims.

Those skilled in the art will recognize that the methods and systems of the present invention have many applications, may be implemented in many manners and, as such, is not to be limited by the preceding exemplary embodiments and examples. Additionally, the functionality of the components of the preceding embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A system for remotely controlling within a body of a patient a catheter having a proximal portion, the system comprising:
    a catheter positioning device comprising:
        a sled member that receives the proximal portion of the catheter, wherein the sled member includes a guidewire control mechanism coupled thereto; and
        a sled base that guides movement of the sled member and the guidewire control mechanism along the sled base towards the body of the patient, wherein the sled base includes a sterile barrier comprising a resealable delivery channel coupled to the sled base and that receives and guides the catheter; and
    a remote controller that receives user input and send commands to the catheter positioning device,
    wherein the guidewire control mechanism controls a speed at which the guidewire is drawn through the catheter and away from the body of the patient to be the same as a speed at which the catheter advances as the sled member moves along the sled base.

2. The system of claim 1, wherein the sled member is configured to receive the proximal portion of the catheter via a modular plate coupled to the sled member.

3. The system of claim 2, wherein the modular plate comprises a gear configured to translate at least one clamp on the modular plate to move an actuator on the proximal portion of the catheter.

4. The system of claim 1, wherein the guidewire control mechanism is configured to advance the guidewire through the catheter.

5. The system of claim 1, wherein the guidewire control mechanism is configured to remove the guidewire from the catheter.

6. The system of claim 1, wherein the guidewire control mechanism comprises at least one roller configured to engage the guidewire.

7. The system of claim 1, wherein the guidewire control mechanism comprises a spool.

8. The system of claim 1, wherein the guidewire control mechanism comprises at least one pulley.

9. The system of claim 1, wherein the sled member comprises a back port through which the guidewire passes.

10. The system of claim 1, further comprising a programmable control system.

11. The system of claim 10, wherein the programmable control system is configured to record movement and positioning of the catheter.

12. The system of claim 10, wherein the programmable control system is configured with preset programs for controlling the catheter.

13. The system of claim 10, wherein the programmable control system is configured to record movement and positioning of the guidewire.

14. The system of claim 10, wherein the programmable control system is configured with preset programs for controlling the guidewire.

* * * * *